US007691564B2

(12) United States Patent
Devreotes et al.

(10) Patent No.: US 7,691,564 B2
(45) Date of Patent: Apr. 6, 2010

(54) HETEROTRIMERIC G-PROTEIN

(75) Inventors: Peter N. Devreotes, Towson, MD (US); Chris Janetopoulos, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/322,648

(22) Filed: Jan. 3, 2006

(65) Prior Publication Data

US 2006/0223115 A1 Oct. 5, 2006

Related U.S. Application Data

(63) Continuation of application No. 09/764,141, filed on Jan. 19, 2001, now abandoned.

(60) Provisional application No. 60/240,709, filed on Oct. 16, 2000.

(51) Int. Cl.
*C12Q 1/00* (2006.01)
*G01N 33/53* (2006.01)
*G01N 33/567* (2006.01)

(52) U.S. Cl. .............................. 435/4; 435/7.1; 435/7.2; 435/7.21; 435/7.6

(58) Field of Classification Search ........................ None
See application file for complete search history.

(56) References Cited

U.S. PATENT DOCUMENTS

| | | | |
|---|---|---|---|
| 5,998,204 A | 12/1999 | Tsien et al. | |
| 6,294,330 B1 | 9/2001 | Michnick et al. | |
| 6,824,990 B1 * | 11/2004 | Blumer ...................... | 435/7.1 |

FOREIGN PATENT DOCUMENTS

| | | |
|---|---|---|
| WO | WO 98/48278 | 10/1998 |
| WO | WO 99/03974 A1 | 1/1999 |
| WO | WO 01/34766 | 5/2001 |
| WO | WO 01/62919 A1 | 8/2001 |

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Overton et al., G-protein-coupled receptors function as oligomers in vivo, Current Biology, Mar. 10, 2000, vol. 10, No. 6, p. 341-344.*
Miyaki et.al., Nature, 1997, 388: 882-887.*
Jin et.al., Mol. Biol. Cell., 1998, 9: 2949-2961.*
Xu et.al., Proc. Natl. Acad. Sci., 1999, 96:151-156.*
Taft et al., Trends in Genetics 22(12):649-653, 2006.*
Linder, Lab. Anim. 30(5):34-39, 2001.*
Bilbo et al., Lab. Anim. 30(1):24-29, 2001.*
Holschneider et al., Int. J. Dev. Neuroscience 18 :615-618, 2000.*
Wood, Comp. Med. 50(1): 12-15, 2000.*
Sigmund, Arterioscler. Throm. Vasc. Biol. 20:1425-1429, 2000.*
Kappel et al., Current Opinion in Biotechnology 3:558-553, 1992.*
Milligan et al. (Heterotrimeric G-proteins: a short history, British Journal of Pharmacology, 147, pp. S46-S55, 2006).*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Antonelli et al. (Human-*Xenopus* chimeras of Gs reveal a new region important for its activation of adenylyl cyclase, FEBS Letters, 340 (1994), pp. 249-254).*
NCBI G protein search results. Retrieved from the Internet <URL:http://www.ncbi.nlm.nih.gov>.*
Liu et al. (The helical domain of a G protein alpha subunit is a regulator of its effector, Proc. Natl. Acad. Sci., vol. 95, pp. 12878-12883, 1998).*
Bevan, Nicola, et al., "Functional analysis of a human A1 adenosine receptor/green fluorescent protein/Gilalpha fusion protein following stable expression in CHO cells", FEBS Letters, Nov. 26, 1999, pp. 61-65, vol. 462, No. 1-2, Elsevier Science Publishers, Amsterdam, NL.
Janetopoulos, Chris, et al., "Receptor-Mediated Activation of Heterotrimeric G-Proteins in Living Cells," Science, Mar. 23, 2001, pp. 2408-2411; vol. 291, No. 5512, Science, Washington, DC.
Jin, Tian, et al., "Localization of the G Protein Betagamma Complex in Living Cells during Chemotaxis," Science, Feb. 11, 2000, pp. 1034-1036, vol. 462, No. 5455, Science, Washington, DC.
Mochizuki, Naoki, et al., "Spatio-temporal images of growth-factor-induced activation of Ras and Rap1", Nature, Jun. 28, 2001, pp. 1065-1068, vol. 411, Macmillian Magazines, Ltd.
Pollok, Brian A., et al., "Using GFP in FRET-based applications," *trends in* Cell Biology, Feb. 1999, pp. 57-60, vol. 9, Elsevier Science, Ltd.
Website, "Fluorescence Resonance Energy Transfer", *Fluorescence Resonance Energy Transfer*, Jun. 2000, pp. 1-3 http://www.probes.com/handbook/sections/0002'.html.
Website, "Green Fluorescent Protein (GFP) and Other Fluorescent Proteins", *Aurora Biosciences Corp.*, pp. 1-7 http://www.aurorabio.com/bioassay/fluorescent.html.
Website, "Fluorescence Resonance Energy Transfer Spectroscopy", *FRET Page*, pp. 1-7 http://www.anatomy.usvd.edu.au/mru/fret/abot.html.
Biondi et al., Nucl. Acids Res. 26: 4946-52 (1998).
Jensen et al., Eur. J. Biochem.269: 5076-87 (2002).
Zeng et al., Mol. Pharmacol. 64: 1474-84 (2003).

(Continued)

*Primary Examiner*—Suzanne M. Noakes
*Assistant Examiner*—Jae W Lee
(74) *Attorney, Agent, or Firm*—Banner & Witcoff, Ltd.

(57) ABSTRACT

Receptor mediated activation of heterotrimeric G-proteins is visualized in living cells by monitoring fluorescence resonance energy transfer (FRET) between subunits of a G protein fused to cyan and yellow fluorescent proteins. The G-protein heterotrimer rapidly dissociates and reassociates upon addition and removal of cognate ligand. Energy transfer pairs of G-proteins enables direct in situ detection and have applications for drug screening and GPCR de-orphaning.

20 Claims, 4 Drawing Sheets

OTHER PUBLICATIONS

Tian et al., Mol. Biol. Cell 9:2949-2961, 1998.
Miyaki et al., Nature 388: 882-887, 1997.
Medina et al., J. Biol. Chem.. 271: 24720-24727, 1996.
Xu et al., Proc. Natl. Acad. Sci. USA 96: 151-156, 1999.
Wall et al. Cell 83: 1047-1058, 1995.
Pfleger et al., "New Technologies: Bioluminescence Resonance Energy Transfer (BRET) for the Detection of Real Time Interactions Involving G-Protein Coupled Receptors," Pituitary 6: 141-151, 2003.

* cited by examiner

HETEROTRIMERIC G-PROTEIN

This application claims the benefit of provisional application Ser. No. 60/240,709 filed 16 Oct. 2000, the contents of which are expressly incorporated herein.

The U.S. government retains certain rights in the invention according to the provisions of grants from the U.S. National Institutes of Health numbered GM28007 and GM34933.

TECHNICAL FIELD OF THE INVENTION

This invention is related to the area of G protein coupled receptors. In particular it relates to means of directly assaying signaling initiated by binding of ligands to G protein coupled receptors.

BACKGROUND OF THE INVENTION

Chemoattractants, hormones, neurotransmitters, odorants and other sensory stimuli exert their effects upon cells through a vast family of serpentine G-protein couple receptors (GPCRs). The mechanisms of G-protein mediated signal transduction have been studied using isolated membranes and purified proteins. These studies have shown that excited receptors catalyze the exchange of GTP for GDP and the dissociation of the G-protein heterotrimer, allowing both the GTP-bound α-subunit and free βγ-complexes to signal to downstream effectors. The intrinsic GTPase activity of the α-subunit hydrolyzes the bound GTP and the heterotrimer reassociates, completing the cycle (1,2). There is a need in the art for a technique to directly monitor subunit dissociation and reassociation in living cells.

SUMMARY OF THE INVENTION

It is an object of the present invention to provide G protein subunits which are fluorescent or luminescent.

It is another object of the present invention to provide G proteins which are capable of fluorescence resonance energy transfer or bioluminescence resonance energy transfer (BRET) from one subunit to another.

It is an object of the present invention to provide nucleic acids which encode G protein subunits which are fluorescent or luminescent.

Another object of the invention is to provide a method for detecting conformational changes in a protein.

Another object of the invention is to provide a method for directly detecting G protein coupled receptor signaling in the presence of a test sample.

Another object of the invention is to provide a functional heterotrimeric G protein capable of fluorescence resonance energy transfer (FRET) or bioluminescence resonance energy transfer (BRET).

Another object of the invention is to provide a functional heterotrimeric G protein capable of fluorescing or luminescing and quenching.

These and other objects of the invention are achieved by providing one or more of the following embodiments. In one embodiment a functional α subunit of a heterotrimeric G protein is provided which comprises an amino acid sequence encoding a fluorescent or luminescent protein.

According to another embodiment, a functional β subunit of a heterotrimeric G protein is provided. It comprises an amino acid sequence encoding a fluorescent or luminescent protein.

Another embodiment of the invention provides a functional heterotrimeric G protein comprising an α subunit comprising a first amino acid sequence encoding a first fluorescent or luminescent protein and a β or γ subunit comprising a second amino acid sequence encoding a second fluorescent or luminescent protein. The first and second fluorescent or luminescent proteins are capable of fluorescence resonance energy transfer (FRET) or bioluminescence resonance energy transfer (BRET).

According to another aspect of the invention a nucleic acid encoding a functional α subunit of a heterotrimeric G protein is provided. It comprises an amino acid sequence encoding a fluorescent or luminescent protein.

Another aspect of the invention is a nucleic acid encoding a functional β subunit of a heterotrimeric G protein. It comprises an amino acid sequence encoding a fluorescent or luminescent protein.

In another embodiment of the invention a eukaryotic cell is provided. It comprises: (a) a nucleic acid encoding a functional α subunit of a heterotrimeric G protein which comprises an amino acid sequence encoding a first fluorescent or luminescent protein; and (b) a nucleic acid encoding a functional β of γ subunit of a heterotrimeric G protein which comprises an amino acid sequence encoding a second fluorescent or luminescent protein. The eukaryotic cell expresses a G protein which is capable of FRET or BRET.

Yet another embodiment of the invention provides a method for detecting conformational changes in a protein. Changes in fluorescent resonance energy transfer (FRET) of an artificial protein subjected to a change in environmental conditions are detected. The artificial protein comprises at least two subunits. A first subunit comprises a cyan fluorescent protein and a second subunit comprises a yellow fluorescent protein. The cyan fluorescent protein and the yellow fluorescent protein are within 100 angstroms of each other. A change in FRET indicates that the change in environmental conditions caused the artificial protein to change its conformation.

According to still another embodiment of the invention a functional heterotrimeric G protein is provided. It comprises an α subunit comprising a first fluorescent or luminescent moiety and a β or γ subunit comprising a second fluorescent or luminescent moiety. The first and second fluorescent or luminescent moieties are capable of fluorescence resonance energy transfer (FRET) or bioluminescence resonance energy transfer (BRET).

According to still another aspect of the invention a functional heterotrimeric G protein is provided. It comprises an α subunit comprising a fluorescent or luminescent moiety and a β or γ subunit comprising a quenching moiety. The quenching moiety is capable of quenching fluorescence of the fluorescent moiety or the luminescence of the luminescent moiety.

Another aspect of the invention is a functional heterotrimeric G protein which comprises an α subunit comprising a quenching moiety and a β or γ subunit comprising a fluorescent or luminescent moiety. The quenching moiety is capable of quenching fluorescence of the fluorescent moiety or the luminescence of the luminescent moiety.

Still another embodiment of the invention provides a functional γ subunit of a heterotrimeric G protein. The G protein comprises an amino acid sequence encoding a fluorescent or luminescent protein.

Still another aspect of the invention is a nucleic acid encoding a functional γ subunit of a heterotrimeric G protein. It comprises an amino acid sequence encoding a fluorescent or luminescent protein.

These and other embodiments of the invention provide the art with a means for assessing G protein signaling in situ in cells.

BRIEF DESCRIPTION OF THE DRAWINGS

FIGS. 1A to 1D. Functional interaction of G β-YFP and G α2-CFP in living cells. (FIG. 1A) Model depicting the arrangement of CFP and YFP. CFP was inserted into the helical domain of G α2 in a location optimal for FRET with YFP fused to the N-terminal of G β (FIG. 1B) Expression of G β-YFP and G α2-CFP protein. Lysates of G α2⁻(1), wild-type (2), G α2-CFP/g α2⁻ (3), α2-CFP: β-YFP cells (4), g β-cells (5), and G β-YFPgβ⁻ cell lines (6) were subjected to immunoblot analyses. G α2antisera detect an appropriate band in wild-type cells (not shown) and a band at 72 kD in the G α2-CFP/gα2⁻ and α2-CFP: α-YFP cells. Antisera against GFP (Clontech) recognize the G α2-CFP band at 72 kD in the G α2-CFP/g α2⁻ cells, a doublet of the 72 kD band and a 70 kD band of G β-YFP in the α2-CFP: β-YFP cells, and the 70 kD band in the G β-YFPgβ⁻ cells. (FIG. 1C) In vivo Actin polymerization assays of gα2⁻ (light grey), wild-type (black), and α2-CFP: β-YFP (dark grey) cells were carried out as previously described (35). Cells were stimulated with 100 nM cAMP at t=0 and fixed at times shown. Mean values for an experiment done in duplicate are shown. Two other independent experiments were performed and yielded similar results. (FIG. 1D) Chemotaxis of α2-CFP: β-YFP cells. Cells were differentiated with repeated cAMP stimuli for 6 hours then examined for chemotactic response in a micropipette assay. At time 0, a micropipette was filled with 1:M cAMP and placed on the surface of the coverglass. The positions at time 0 and 10 mm are shown. Bar is 10:m.

FIGS. 2A to 2E. Fluorescence spectra of cell lines. (FIG. 2A) Developed cells were excited in a Spex Fluoromax-2 fluorimeter at 440 nm and emission was collected between 460 nm and 600 nm and processed as described (14). Gα2-CFP/g α2⁻ cells ("α2-CFP"), α2-CFP: β-YFP cells ("α2-CFP: -YFP"), and mixture of equal number of Ga-2-CFP/gα2⁻ and G β-YFP/g βcells ("mixed cells"). (FIG. 2B) Emission spectra from α2-CFP: β-YFP cells before and after treatment with 100:M cAMP. (FIG. 2C) Kinetics of transient loss of FRET after addition of 100:M cAMP to α2-CFP: β-YFP cells (36). Cells were scanned at selected time points following addition of the stimulus. (FIG. 2D) Cells were observed with an excitation and emission bandpass filters of 420 nm to 450 nm (Chroma Exciter 436/20) and 520 nm to 550 nm (Chroma Emitter 535/30), respectively. Mean intensities were calculated in IPLab Spectrum by manually circumscribing the membrane of multiple cells. The three curves represent individual cells from three different video sequences. Arrows indicate the frame at which the stimulus was added. (FIG. 2E) Difference images of consecutive frames of one captured at 3 second intervals were calculated in IPLab Spectrum. Stimulus was added between frames labeled 0 and 3 seconds; small cell indicated by the arrow was dislodged by the disturbance. Calibration bar is 10 μm.

FIGS. 3A to 3B. Dose-response curves for cAMP, 8-Br cAMP, and 2'H cAMP.

FIGS. 4A to 4C. Continuous activation of the G-protein cycle. (FIG. 4A) α2-/CFP:β-YFP cells were treated with 3 mM caffeine, adjusted to 100 nM cAMP every minute for 20 minutes, then divided into two sets. One set received no further cAMP, while the second was adjusted and held at 10 mM cAMP. (FIG. 4B) Receptor regulation of PH domain translocation. Cells were treated with cAMP for 0 or 15 minutes, lysed, and then incubated in the presence or absence of GTPγS with a supernatant from cells expressing $PH_{CRAC}$-GFP. After 2 minutes membranes were collected and binding of the $PH_{CRAC}$-GFP was assessed by immunoblot analysis using antibodies to GFP (22). (FIG. 4C) Assessment of cAR1 phosphorylation. Immunoblot analysis shows separation of the cAR1 doublet into its higher (phosphorylated) and lower (non-phosphorylated) mobility forms (23).

DETAILED DESCRIPTION

It is a discovery of the present invention that artificial heterotrimeric G protein derivatives can be constructed and can be used to directly monitor G protein coupled receptor signaling in cells or in cell components. Such artificial proteins can be made by genetic engineering, fusing together two amino acid sequences not naturally present in the same protein. The basic structure is a natural G protein. To this protein either a fluorescent or luminescent amino acid sequence can be added or a tagging sequence can be added. The tagging sequence permits non-proteinaceous fluorescent or luminescent moieties or quenching moieties to bind at a particular location in a protein. It has been found that upon GPCR signaling, conformational changes in G proteins can be detected by monitoring changes in G proteins which are modified to be fluorescent or luminescent. The artificial G proteins retain their catalytic abilities. Preferably the artificial G proteins are capable of FRET or BRET. Alternatively they both fluoresce and quench depending on the conformation of the molecule. Monitoring can be accomplished using a fluorescence spectrophotometer.

G proteins typically have an α, a β, and a γ subunit. GPCR catalyzes the dissociation of α from βγ. The β and γ subunit form a subcomplex which stays intact even during signaling. After cleavage of cGMP by the α subunit, the three subunits reassociate. A fluorescent or luminescent amino acid sequence can be incorporated into any of the three subunits. Preferably the amino acid sequence is at the N-terminus of the β or γ subunit, and in the helical domain of the α subunit. More preferably the amino acid sequence is between the αA and the αB helices or the αB and αC helices of the α subunit. Other positions within the helical domain can also be used. Two preferred fluorescent amino acid sequences are cyan fluorescent protein and yellow fluorescent protein. When maintained within a distance of about 10-100 angstroms these two proteins are capable of FRET. Particularly preferred G proteins are those of *D. discoideum* and more particularly the Gα2, protein. Any eukaryotic G proteins can be used, however, including bovine, human, murine, rat, and ovine. Any fluorescent or luminescent proteins or moieties can be used which are capable of FRET, including GFP from the jellyfish *Aequorea victoria* and its variants CFP and YFP. In general, two moieties can participate in FRET when the fluorescence emission spectrum of the donor overlaps with the adsorption spectrum of the acceptor. In addition, the transition dipole orientations must be approximately parallel.

In addition, the closely related technique of bioluminescence resonance energy transfer (BRET) can be used. The α- or βγ-subunits can comprise a light-emitting luciferase protein moiety that can excite a fluorescent protein moiety on the complementary subunit.

Nucleic acids encoding an artificial α, β, and/or γ subunits of a heterotrimeric G protein are also provided. These nucleic acids encode an amino acid sequence encoding a fluorescent or luminescent protein fused to a G protein subunit. The nucleic acids are not naturally occurring. They can be creating by cloning or chemical synthesis or PCR amplification using particular primers. Many such methods are known in the art and any can be used as is convenient.

Eukaryotic cells can be used for measuring and monitoring G protein coupled receptor signaling. Such cells can be of any species, from mammals such as rats, mice, horses, cows, and humans to single celled organisms, fungi and molds. Such cells will preferably comprise one or more nucleic acids encoding a functional α subunit of a heterotrimeric G protein which comprises an amino acid sequence encoding a first fluorescent or luminescent protein and a nucleic acid encoding a functional β of γ subunit of a heterotrimeric G protein which comprises an amino acid sequence encoding a second fluorescent or luminescent protein. The two amino acid sequences will be able to FRET or BRET. It is desirable that the eukaryotic cell also express a G protein coupled receptor. Typically this will be due to expression of an exogenous sequence which has been added to the cell so that the G protein coupled receptor is expressed in the eukaryotic cell. Alternatively, the cell may be one which naturally expresses a G protein coupled receptor. Any eukaryotic cell can be used as is convenient for the particular purpose of the method. Some examples of cells which can be used are $S.$ $cerevisiae$, $D.$ $discoideum$, HEK 293, CHO, and NIH 3T3 cells. Any G protein coupled receptor can be used as is appropriate for the particular purpose. Suitable receptors are those whose ligands include but are not limited to those for chemoattractants, odorants, hormones, and neurotransmitters.

The ability to use FRET to monitor changes in protein conformation is not limited to G proteins and G protein coupled receptors. Any protein can be monitored for a change in conformation that changes the distance between subunits from a FRET enabling distance to a FRET disabling distance or visa versa. Typically the distance which enables FRET is less than 100 angstroms. One subunit can comprise a cyan fluorescent protein and a second subunit can comprise a yellow fluorescent protein to form an artificial form of the protein which is fluorescent tagged. After subjecting the artificial protein to a change in environmental conditions, a change in FRET indicates that the change in environmental conditions caused the artificial protein to change its conformation. Environmental conditions which can be changed are temperature, ligand or substrate concentration, radiation, solvent, inhibitor concentration, cofactor concentration, etc. Artificial proteins suitable for such methods can be made using recombinant DNA techniques to form the fusion proteins as subunits of the artificial proteins.

The invention provides a number of advantages. Assays can be done in intact, living cells. The cells can be in culture, in tissues, or in a whole organ. The ability to use whole cells provides additional physiological inputs which may not be possible in cell-free systems. In addition, the method is fast, allowing real-time measurements to be obtained. The invention also allows the direct monitoring of the first step of the signal transduction pathway and does not rely on subsequent downstream signaling events. Importantly, the response is directly proportional to and dependent on the concentration of applied stimulus. The artificial proteins of the invention can also be assayed in cell-free systems, if that is desirable for a particular applications.

As mentioned above, tagging sequences can be added to the subunits of the heterotrimeric G proteins which permit the labeling by non-proteinaceous fluorescent moieties. Thus the moieties are targeted for the tagging sequences in the subunits. Such moieties can be either fluorescent or luminescent or quenching. Thus either FRET or quenching can be monitored when using such artificial proteins which are labeled with moieties. The placement of the tags follow the same guidelines as the placement of the fluorescent or luminescent amino acid sequences within the subunits as discussed above. Typically the moieties will be within 100 angstroms of each other to have either a FRET or quenching effect.

Conformation as used in the present invention denotes the combination of secondary, tertiary, and quaternary structure of proteins. Thus any change in any of these aspects of protein structure can lead to the separation of two moieties beyond the distance that they can effectively participate in FRET or quenching. Typically G protein subunits dissociate to α subunits and a βγ complex during signaling, and this is sufficient to cause a decrease in FRET.

Because of the highly conserved structures of the heterotrimeric G-proteins, the method of the invention is applicable to any member of the heterotrimeric G-protein super family. We have demonstrated that insertion of a fluorescent or luminescent protein within the helical domain of the α-subunit does not interfere with its function and places it into a position to favorably interact with a complementary fluorescent protein fused to the N-terminal of the β-subunit. Construction of similar energy transfer pairs with each of the mammalian G-proteins permits direct in vivo measurements of G-protein mechanisms and provides a readout of the activation of any G-protein coupled receptor in situ. Applications for assays employing such fluorescent G protein subunits include screening for novel drugs or novel uses of old drugs, GPCR de-orphaning (i.e., determining what ligands activate GPCRs for which no ligands are known), as well as studies of multiple stimulus processing, olfactory coding, and neuronal circuits.

Any suitable heterotrimeric G protein can be used according to the invention, deriving from any eukaryotic species. The tremendous conformational conservation of this superfamily of proteins is demonstrated by the successful use of the crystal structures of bovine G proteins to design structures for G protein of the amoeba $D.$ $discoideum$. Any mammalian G proteins can be used, including but not limited to those of rat, mouse, goat, sheep, cow, human, monkey, gibbon, and ape.

While applicants have demonstrated the operability of the invention using genetic fusion proteins, it is contemplated that covalently labeled G proteins can be used, for example, using FLASH and variants of FLASH, a commercially available fluorescent compound that targets to a specific engineered sequence. Like the β subunit which has been labeled in the N-terminus, the γ subunit can also be N-terminally labeled and paired with correspondingly labeled α subunits. While applicants have demonstrated that α subunits can be labeled between the αA and the αB helices, they can also be labeled in amino acid positions near these helices, and possibly to other regions within the helical domain between αB and αC. The critical parameter is that the fluorescence tags must be in sufficiently close apposition such that quenching or FRET is possible. A distance of 100 angstroms is typically sufficiently close to accomplish this function.

Assays according to the present invention are preferably done in living cells. However, cell-free assays can also be performed. These can utilize either membrane fractions or supernatant fractions, as G proteins have been found in both fractions. Those of skill in the art can readily make such fractions according to techniques well known in their respective fields.

G protein coupled receptors suitable for use in the present invention include chemoattractants, odorants, hormones, and neurotransmitters.

The above disclosure generally describes the present invention. A more complete understanding can be obtained by reference to the following specific examples which are provided herein for purposes of illustration only, and are not intended to limit the scope of the invention.

EXAMPLE 1

Gα2 and G β of *D. discoideum* were tagged with cyan and yellow fluorescent proteins used FRET to observe the state of the G-protein heterotrimer in living cells (7).

Figure 1:
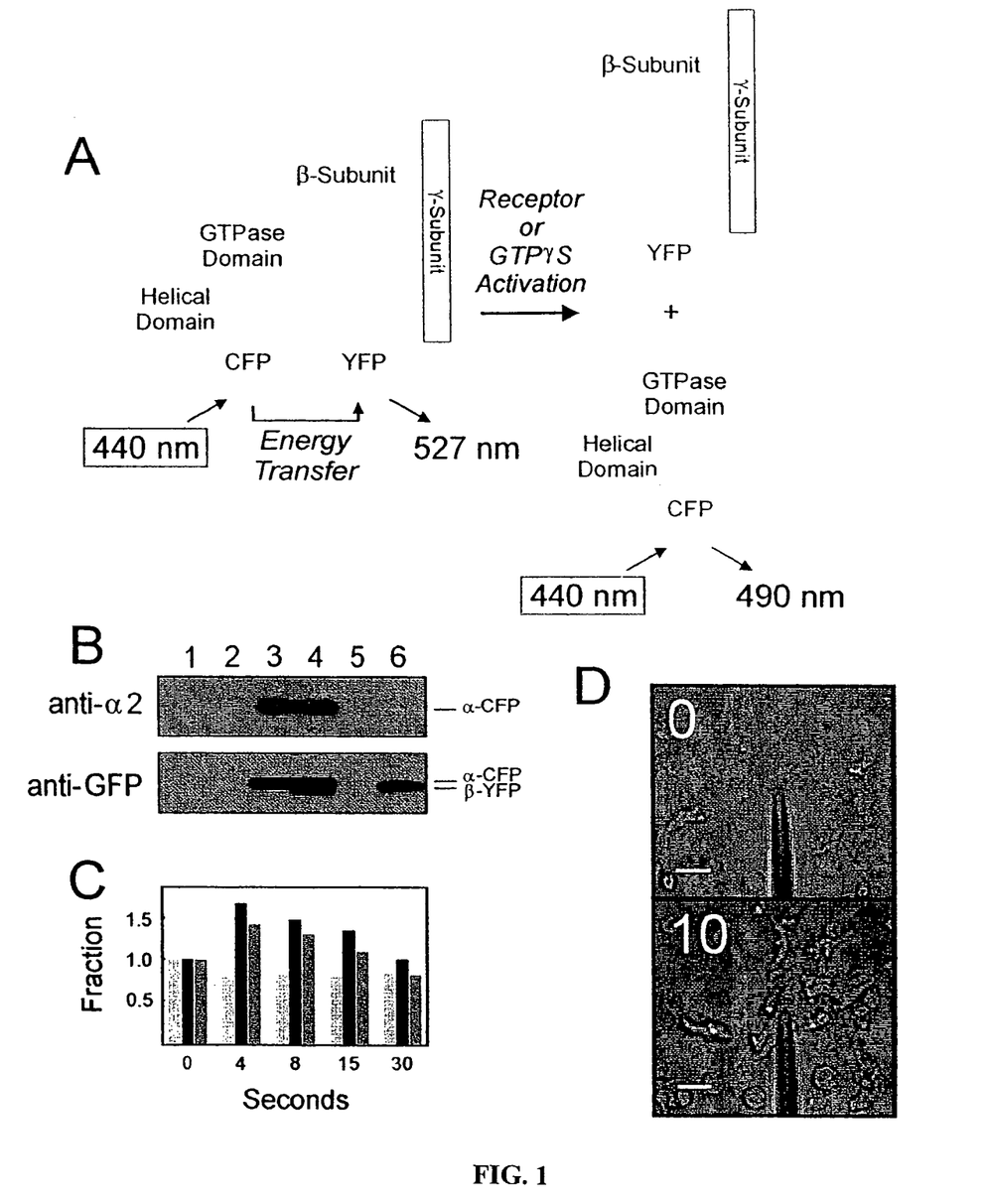

We assessed the activities of the fusion proteins by phenotypic rescue of Gα2 and Gβ null cell lines. Fusion of enhanced yellow fluorescent protein (YFP) to the amino terminus of Gβ does not impair the capacity of Gβ to rescue the chemotactic defects of Gβ null mutants (gβ cells) (6,8). Guided by the crystal structures of several mammalian heterotrimers (9,10), we inserted the enhanced cyan fluorescent protein (CFP) into the first loop (between αA and αB).of the helical domain of Gα-2. Mutants that do not express Gα2 (gα2⁻ cells) are completely deficient in chemoattractant-induced responses and therefore are unable to aggregate and differentiate (11). Stable expression of Gα2-CFP rescued the chemotactic and developmental defects of the gα2⁻ cells (12). Chemoattractants triggered in vivo actin polymerization and chemoattractant-filled micropipettes induced chemotactic responses. Similarly, co-transformation with Gα2-CFP and Gβ-YFP rescued the gα2⁻ cells (FIG. 1)(13).

EXAMPLE 2

Figure 2:
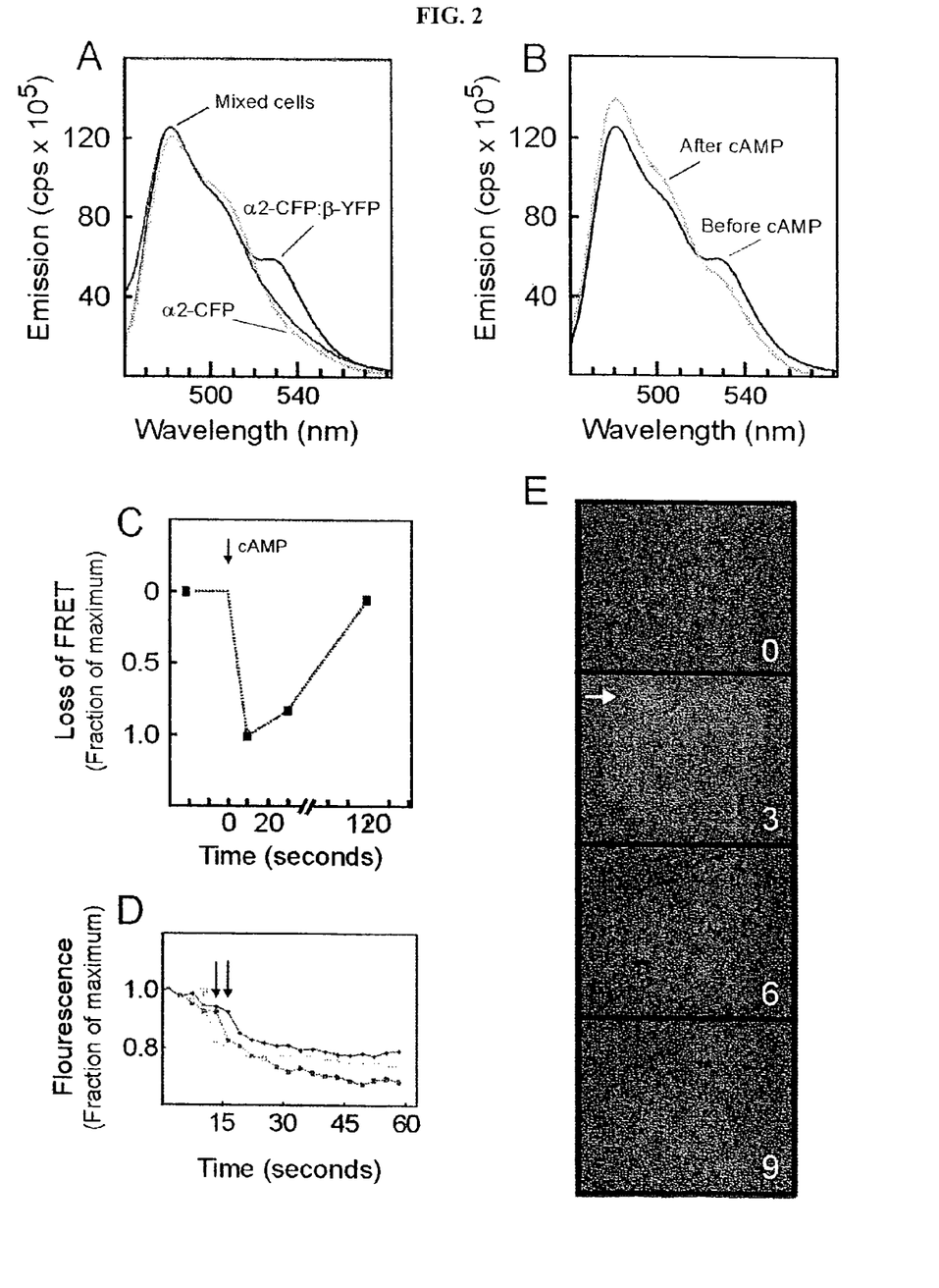

Cell lines expressing fluorescent subunits showed direct, specific transfer of resonate energy from Gα2-CFP to Gβ-YFP when the two proteins were co-expressed (FIG. 2A).

We excited living, differentiated cells at 440 nm and recorded the emission spectrum between 460 and 600 nm. The co-transformed cells showed an extra peak near 527 nm, indicating FRET. Cell lines expressing Gα2-CFP alone or mixtures of cells containing either Gα2-CFP or Gβ-YFP alone did not display this signal. Calculations of FRET efficiency varied from 7% as in the experiment in FIG. 2 to 12% in other experiments (14). The high efficiency of energy transfer, considering that at least 50% of the Gβ molecules are not fused to YFP, suggests that most of the G-protein molecules are in the heterotrimeric state in resting cells. Co-transformation of Gα2-CFP and Gβ-YFP into gβ cells gave similar results; this study focused on the co-transformed gα2⁻ cells (designated α-CFP: β-YFP cells). The signal was retained in both membrane and supernatant fractions prepared from α-CFP: β-YFP cells, suggesting heterotrimers exist in the cytoplasm as well as on the plasma membrane. The FRET signal disappeared following treatment of membranes with Mg⁺⁺ plus GTPγS, but not with GTPγS alone (data not shown).

EXAMPLE 3

Addition of the chemoattractant, cyclic adenosine 3', 5' phosphate cAMP),to α-CFP: β-YFP cells triggered a rapid, substantial loss of FRET due to receptor-mediated activation of the G-protein heterotrimer (FIG. 2B). There was a decrease in the YFP emission signal near 527 nm and a parallel increase in the CFP emission signals near 475 and 501 nm. The 490: 527 ratio increased by 32%; the FRET signal decreased by approximately 70% (15). Only α-CFP: β-YFP cells showed a change in fluorescence intensity when stimulated. The large decrease suggests that the heterotrimer may dissociate rather than merely change conformation. The kinetics of loss and restoration of FRET upon addition and removal of the stimulus are shown in FIG. 2C. The response was maximal within 10 seconds of stimulation, the earliest time point taken. In other experiments, the response reached 90% of the maximum within a few seconds (data not shown). As the cAMP was removed by the endogenous phosphodiesterase (PDE), the FRET signal returned to its maximal level within two minutes. Activation is at least as fast as the most rapid receptor-mediated physiological responses such as actin polymerization and PH domain translocation.

EXAMPLE 4

This example demonstrates the direct visualization of the change in the FRET signal by conventional fluorescence microscopy. As shown in FIG. 2D and E, when α-CFP: β-YFP was excited with blue light (420 to 460 nM) and observed in the yellow range (525 to 540 nM), there was a fluorescent signal on the membrane as well as within the cell perimeter. These FRET signals were lower in cells expressing α2-CFP or β-YFP alone even though these cells were highly fluorescent when examined with the appropriate cyan or yellow filter sets. When a saturating dose of cAMP was added to the α-CFP: β-YFP cells, the membrane signal decreased by about 15% within 6 seconds and did not reappear during the one minute period of observation. The signal within the perimeter of the cell also displayed a slight decrease. We processed the response by taking differences of consecutive frames as shown in FIG. 2E. Ratio and confocal imaging can be used to enhance these responses and to determine whether a portion of the signal represents cytosolic G-protein. These microscopy results extend and confirm the fluorometric observations.

EXAMPLE 5

Figure 3:
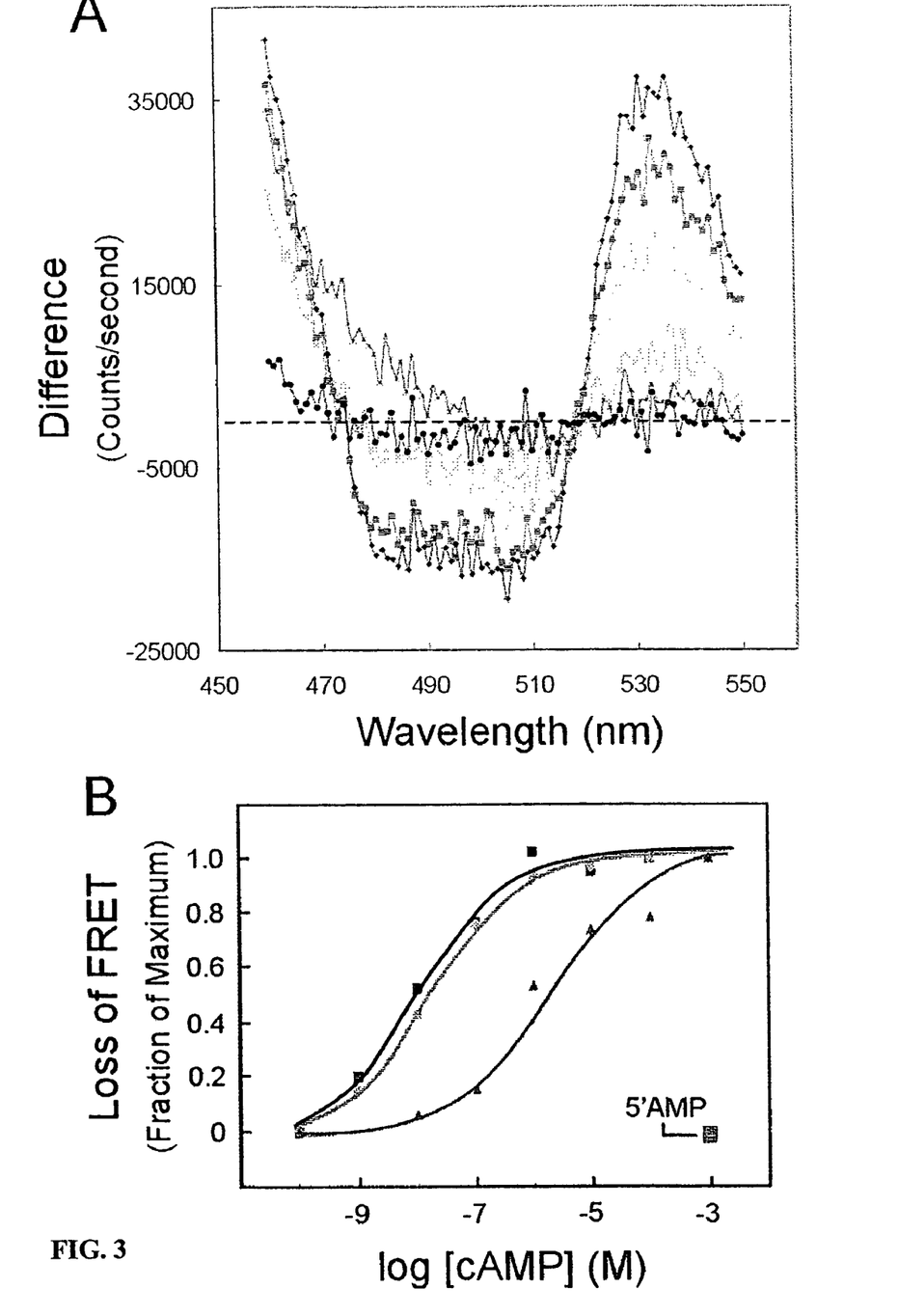
(FIG. 3A) Fluorescence spectrum of α2-CFP: β-YFP cells treated with increasing concentrations of cAMP. Cells were treated with caffeine and stimulated with 0, 1 nM, 10 nM, 100 nM, 1 μM, 10 μM, and 100 μM cAMP in the presence of 10 mM dithiothreitol, mixed, and analyzed immediately in the fluorimeter. Data was processed as described (34).
(FIG. 3B) Dose-response curves for cAMP (black), 2'H cAMP (light grey), and 8-Br cAMP (dark grey), and 5' AMP. Data from two independent experiments were averaged for each curve.

Treatment with increasing concentrations of cAMP and two of its analogues, 2'-dcAMP and 8-Br-cAMP decreased the FRET signal in a dose-dependent manner (FIG. 3). To quantitate the response for each analog, we subtracted the spectrum for the highest concentration from that of each of the lower concentrations. The negative values from 475 to 520 nm reflected the gain in cyan fluorescence and the positive values from 520 to 550 nm reflected the loss in yellow fluorescence (3A and see 2B). Processing of this data yielded $EC_{50}$s for cAMP, 2'-dcAMP, and 8-Br-cAMP of about 10 nM, 20 nM and 2 μM, respectively, which were shifted to the left of their reported binding affinities (average $K_DS$≈180 nM, 1 μM and 32 μM, respectively) (16). This suggests that the steady-state level of G-protein activation saturates before receptor occupancy and favors the possibility that the receptors act catalytically. Addition of 1 mM 5'-AMP, which does not bind to cAR1, had no effect on the FRET signal. These data validate the hypothesis, based on previous genetic studies (11), that the heterotrimeric G-protein formed from Gα2, one of 11 known α-subunits in *D. discoideum* (17,18), and the unique βγ-complex are directly linked to the cAMP chemoattractant receptors.

Figure 4:
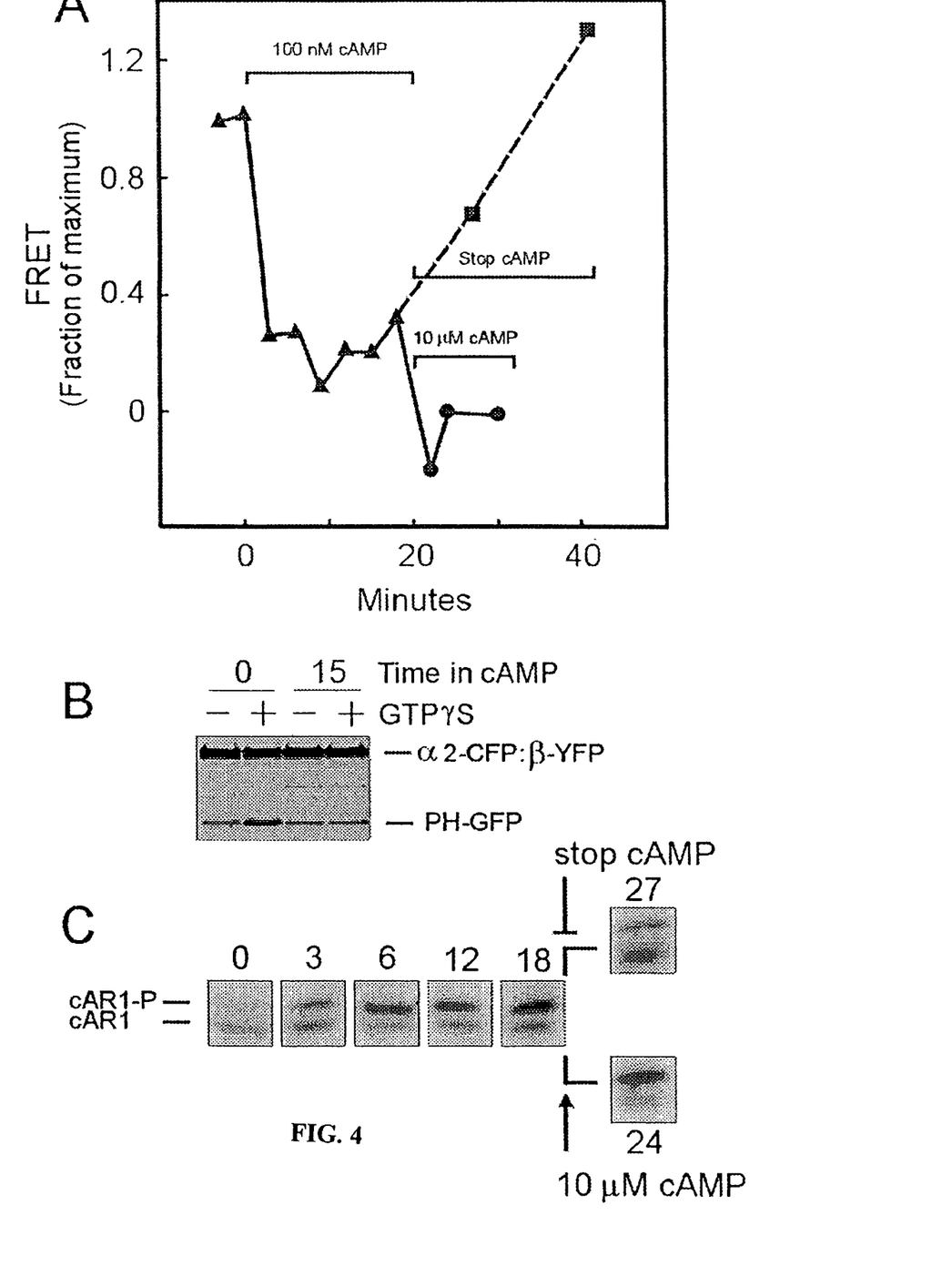

Prolonged stimulation of *D. discoideum* cells with cAMP induces adaptation of a number of physiological responses, such as actin polymerization and PH-domain recruitment to the plasma membrane (19). Yet previous studies have suggested that receptors remain coupled to G-proteins in adapted cells (20). To examine adaptation of the G-protein heterotrimer, we persistently stimulated α2-CFP: β-YFP cells with 100 nM cAMP for 20 minutes, divided the cells, left one set to recover, and adjusted the other to 10 µM cAMP. During the first 20 minutes of treatment, the FRET signal in living cells decreased and remained near 20% of the initial value (FIG. 4) (21). Cells that received no cAMP after 20 minutes showed a gradual increase in FRET, reflecting the gradual degradation of cAMP by endogenous phosphodiesterase. Cells treated with 10 µM cAMP showed a further decrease in FRET. We used a previously established assay to assure that α2-CFP:β-YFP cells displayed normal adaptation (22,23). In lysates from naive cells, GTPγS stimulated the binding of PH-domains to membranes; this response was lost in the adapted cells (FIG. 4B). Since persistent stimulation does not return the G-proteins to the heterotrimeric or "off" position, adaptation of the physiological responses must occur at another point in the signaling pathway.

The persistent activation of the G-protein cycle is surprising since agonist-induced phosphorylation of the receptors reaches a plateau within a few minutes. Immunoblots of selected time points showed the expected steady-state level of receptor phosphorylation (FIG. 4C). Previous studies have shown that phosphorylation of cAR1 at serines 303 and 304 decreases its affinity for cAMP by 5-fold (24); however, the low affinity receptors continue to trigger the G-protein cycle. We are currently designing experiments to test whether the $EC_{50}$ of the G-protein activation shifts higher when receptors are phosphorylated. Agonist induced phosphorylation of other GPCRs facilitates a series of events, such as arrestin binding, that uncouple excited receptors from G-proteins (25-28).

The evidence presented here is consistent with the model of the steady-state G-protein cycle derived from in vitro measurements (1). The rapid kinetics and dose-dependence suggest that occupied receptors repeatedly elicit G-protein activation. Accurate measurements of the rate constants, which will require techniques for rapid mixing or release of caged agonists, will allow quantitation of the parameters of the cycle in vivo. It is expected that regulators of G-protein signaling (RGS proteins) will influence the steady-steady ratio of active and inactive G-protein (29,30); this can now be examined in vivo. Since adaptation does not directly involve the G-protein cycle, RGS proteins must not shape the time courses of the physiological responses.

We are currently determining the localization of G-protein activation when cells are placed in chemoattractant gradients. The persistent kinetics of the activation suggests that its spatial pattern will reflect the shallow external gradient of receptor occupancy rather than the tightly restricted localization of the physiological responses. We have proposed that directional sensing depends on a balance between local excitatory and global inhibitory processes (31). The time course of the G-protein protein activation described here is consistent with the excitatory process, which rapidly reaches a steady state during persistent stimulation. Thus, restriction of the response to the cell's leading edge may involve pathways beyond or independent from the G-protein cycle.

REFERENCES AND NOTES

1. A. G. Gilman, *Annu Rev Biochem* 56, 615-49 (1987).
2. H. E. Hamm, *J Biol Chem* 273, 669-72 (1998).
3. C. A. Parent, B. J. Blacklock, W. M. Froehlich, D. B. Murphy, P. N. Devreotes, *Cell* 95, 81-91 (1998).
4. Z. Xiao, N. Zhang, D. B. Murphy, P. N. Devreotes, *J Cell Biol* 139, 365-74 (1997).
5. G. Servant et al., *Science* 287, 1037-40 (2000).
6. T. Jin, N. Zhang, Y. Long, C. A. Parent, P. N. Devreotes, *Science* 287, 1034-6 (2000).
7. R. Heim, R. Y. Tsien, *Curr Biol* 6, 178-82 (1996).
8. The coding region of the β-YFP fusion protein was cloned into the CV5 vector. CV5 was derived from p88 by addition of an actin 15/expression cassette from pMC34 (3).
9. D. G. Lambright et al., *Nature* 379, 311-9 (1996).
10. M. A. Wall et al., *Cell* 83, 1047-58 (1995)
11. A. Kumagai et al., *Cell* 57, 265-75 (1989).
12. The gene encoding CFP was inserted into a Spe1 site after residue 90, in the loop between the αA and the αB helices, of the Gα2 cDNA. The Spe1 site also added a threonine and serine residue at the N and C terminal loundaries of the insertion. This fusion was cloned into the CV5 vector. The gα2⁻ cells were transformed, and individual G418 resistant clones were selected. Rescued cells formed fruiting blodies and viable spores.
13. Equal amounts of plasmids carrying the Gα2-CFP and Gβ-YFP fusions were mixed, transformed into gα2 cells, and individual G418 resistant clones were selected. Greater than 90% expressed both proteins.
14. The magnitude of the FRET fluorescence compared to that of Gβ-YFP directly excited at 490 nm and not relayed through Gα2-CFP varied from 7% (FIG. 2) to 12%. Emission spectra were collected between 460 and 600 nm (excitation at 440 nm) of the following lines: α2-CFP:β-YFP, a mixture of Gα2-CFP/g α2⁻ and Gβ-YFP/gβ⁻, and wild-type, AX3. Spectra were normalized to the fluorescence at 600 nm of the α2-CFP:β-YFP cells and the wild-type spectrum was subtracted from each of the others. The corrected spectra were normalized to the fluorescence at 490 nm of the α2-CFP:β-YFP cells. The amount of FRET fluorescence was determined by subtracting from the spectrum of the α2-CFP:β-YFP cells either the spectrum of the mixed cells or that of the Gα2-CFP/g α2⁻cells. In the latter case, a further correction was made for the fluorescence emitted from Gβ-YFP/g β⁻ directly excited at 440 nm.
15. The residual signal may be due to cytoplasmic heterotrimer or a portion of membrane associated heterotrimer that remains during persistent stimulation.
16. R. L. Johnson et al., *J Bio Chem* 267, 4600-7 (1992).
17. L. J. Wu, P. N. Devreotes, *Biochem Biophys Res Commun* 179, 1141-7 (1991).
18. S. van Es, P. N. Devreotes, *Cell Mol Life Sci* 55, 1341-51 (1999).
19. C. A. Parent, P. N. Devreotes, *Annu Rev Biochem* 65, 411-40 (1996).
20. B. E. Snaar-Jagalska, S. Van Es, F. Kesbeke, P. J. Van Haastert, *Eur J Biochem* 195, 715-21 (1991).
21. In another experiments, we added a single dose of 100 mM cAMP plus dithiothreitol to inhibit phosphodiesterase. Activation did not subside during 6 minutes of observation.
22. P. J. Lilly, P. N. Devreotes, *J Cell Biol* 129, 1659-65 (1995).
23. R. A. Vaughan, P. N. Devreotes, *J Bio Chem* 263, 14538-43 (1988).
24. M. Caterina, P. N. Devreotes, J. Borleis, and D. Hereld, *J Biol Chem* 270, 8667-8672 (1995).
25. A. Mendez, N. V. Krasnoperova, J. Lem, J. Chen, *Methods Enzymol* 316, 167-85 (2000).
26. J. Chen, C. L. Makino, N. S. Peachey, D. A. Baylor, M. I. Simon, *Science* 267, 374-7 (1995).
27. J. Vinos, K. Jalink, R. W. Hardy, S. G. Britt, C. S. Zuker, *Science* 277, 687-90 (1997).
28. R. R. Gainetdinov et al., *Neuron* 24, 1029-36 (1999).
29. L. De Vries, B. Zheng, T. Fischer, E. Elenko, M. G. Farquhar, *Annu Rev Pharmacol Toxicol* 40, 235-71 (2000).

30. D. M. Berman, A. G. Gilman, *J Bio Chem* 273, 1269-72 (1998).
31. C. A. Parent, P. N. Devreotes, *Science* 284, 765-70 (1999).
32. S. H. Zigmond, M. Joyce, J. Borleis, G. M. BokocL, P. N. Devreotes, *J Cell Biol* 138, 363-74 (1997).
33. Cells were scanned between 515 and 540 nm, normalized to the fluorescence at 527 nm of a 460 to 600 nm emission spectrum of α2-CFP:β-YFP cells (no cAMP). Spectra were corrected by subtraction of a normalized wild-type spectrum.
34. Spectra were first normalized to the integral from 475 to 550 nm. The spectrum at the highest dose was then subtracted from each of the other spectra.

We claim:

1. A method for detecting G protein coupled receptor signaling in the presence of a test sample, the method comprising:
    contacting a eukaryotic cell selected from the group consisting of bovine, human, murine, rat, *D. discoideum*, and ovine cells, with a test sample;
    monitoring fluorescence resonance energy transfer (FRET) or bioluminescence resonance energy transfer (BRET) in said cell, wherein the eukaryotic cell comprises:
        (a) a nucleic acid encoding a first fusion protein comprising an α subunit of a heterotrimeric G protein of the eukaryotic cell, wherein a first fluorescent or luminescent protein moiety is inserted between αA and αB helices, or αB and αC helices of the helical domain of said α subunit; and (b) a nucleic acid encoding a second fusion protein comprising a β or γ subunit of the heterotrimeric G protein fused at its N-terminus to a second fluorescent or luminescent protein moiety,
    wherein the cell expresses a G protein coupled receptor and said first and second fusion proteins and a β or γ subunit of the heterotrimeric G protein which is not part of the first or second fusion protein, wherein said first and second fusion proteins and said β or γ subunit of the heterotrimeric G protein which is not part of the first or second fusion protein form a heterotrimeric G protein comprising an α, β, and γ subunit, wherein the heterotrimeric G protein so formed is capable of binding to said G protein coupled receptor and is capable of FRET or BRET between said first and second fusion proteins;
    observing a change in FRET or BRET between said first and second fluorescent or luminescent protein moieties upon contact with the test sample, which suggests that a component in the test sample binds to and activates the G protein coupled receptor expressed in the cell.

2. The method of claim 1 wherein said first and second fluorescent or luminescent protein moieties are fluorescent.

3. The method of claim 1 wherein said first or second fluorescent or luminescent protein moiety is cyan fluorescent protein.

4. The method of claim 1 wherein the first or second fluorescent or luminescent protein moiety is yellow fluorescent protein.

5. The method of claim 1 wherein said first fluorescent or luminescent protein moiety is cyan fluorescent protein and said second fluorescent or luminescent protein moiety is yellow fluorescent protein.

6. The method of claim 1 wherein said first fluorescent or luminescent protein moiety is yellow fluorescent protein and said second fluorescent or luminescent protein moiety is cyan fluorescent protein.

7. The method of claim 1 wherein said first and said second fluorescent or luminescent protein moieties are within 100 angstroms of each other prior to contacting with the test sample.

8. The method of claim 1 wherein the heterotrimeric G protein is a *D. discoideum* G protein.

9. The method of claim 1 wherein the α subunit of the heterotrimeric G protein is Gα2 of *D. discoideum*.

10. The method of claim 1 wherein the β subunit of the heterotrimeric G protein is Gβ of *D. discoideum*.

11. A method for detecting G protein coupled receptor signaling in the presence of a test sample, the method comprising:
    contacting a eukaryotic cell with a test sample, wherein the eukaryotic cell comprises:
        (a) a first nucleic acid encoding a first fusion protein comprising an α subunit of a *D. discoideum* heterotrimeric G protein, wherein a first fluorescent or luminescent protein moiety is inserted between αA and αB helices, or αB and αC helices of the helical domain of said α subunit; and (b) a second nucleic acid encoding a second fusion protein comprising a β or γ subunit of the *D. discoideum* heterotrimeric G protein fused at its N-terminus to a second fluorescent protein moiety;
    wherein the cell expresses a G protein coupled receptor and said first and second fusion proteins and a β or γ subunit of the heterotrimeric G protein which is not part of the first or second fusion protein, wherein said first and second fusion proteins and said β or γ subunit of the heterotrimeric G protein which is not part of the first or second fusion protein form a heterotrimeric G protein comprising an α, β and γ subunit, wherein the heterotrimeric G protein so formed is capable of binding to said G protein coupled receptor, said first and said second fluorescent protein moieties are within 100 angstroms of each other in said heterotrimeric G protein so formed prior to contacting with the test sample and are capable of fluorescence resonance energy transfer (FRET);
    monitoring FRET in said cell,
    observing a change in FRET between said first and second fluorescent or luminescent protein moieties upon contact with the test sample, which suggests that a component in the test sample binds to and activates the G protein coupled receptor expressed in the cell.

12. The method of claim 11 wherein the α subunit of the heterotrimeric G protein is Gα2.

13. The method of claim 11 wherein the β subunit of the heterotrimeric G protein is Gβ.

14. The method of claim 11 wherein the second nucleic acid encodes a β subunit.

15. The method of claim 1 wherein the eukaryotic cell is human.

16. The method of claim 11 wherein the α subunit of the heterotrimeric G protein is Gα2 and wherein the β subunit of the heterotrimeric G protein is Gβ.

17. A method for detecting G protein coupled receptor signaling, the method comprising:
    monitoring fluorescence resonance energy transfer (FRET) or bioluminescence resonance energy transfer (BRET) in a eukaryotic cell selected from the group consisting of bovine, human, murine, rat, *D. discoideum*, and ovine cells, wherein the eukaryotic cell comprises:
        (a) a nucleic acid encoding a first fusion protein comprising an α subunit of a heterotrimeric G protein of the eukaryotic cell, wherein a first fluorescent or luminescent protein moiety is inserted between αA and αB helices, or αB and αC helices of the helical domain of said α subunit; and (b) a nucleic acid encoding a second fusion protein comprising a β or γ subunit of the heterotrimeric G protein fused at its N-terminus to a second fluorescent or luminescent protein moiety, wherein the cell expresses a G protein coupled receptor and said first and second fusion proteins and a β or γ subunit of the heterotrimeric G protein which is not part of the first or second fusion protein, wherein said first and second fusion proteins and said β or γ subunit of the heterotrimeric G protein which is not part of the first or second fusion protein form a heterotrimeric G protein comprising an α, β, and γ subunit;

monitoring and observing a FRET or BRET signal which is not present in a mixture of the eukaryotic cells in which some cells contain the first fusion protein and some cells contain the second fusion protein but no cells contain both fusion proteins.

18. The method of claim 17 further comprising:
contacting the eukaryotic cell with a test sample;
observing a change in the FRET or BRET signal upon contact with the test sample, which suggests that a component in the test sample binds to and activates the G protein coupled receptor expressed in the cell.

19. The method of claim 17 wherein the eukaryotic cell is human.

20. The method of claim 18 wherein the eukaryotic cell is human.

* * * * *

UNITED STATES PATENT AND TRADEMARK OFFICE
CERTIFICATE OF CORRECTION

| | |
|---|---|
| PATENT NO. | : 7,691,564 B2 |
| APPLICATION NO. | : 11/322648 |
| DATED | : April 6, 2010 |
| INVENTOR(S) | : Peter N. Devreotes and Chris Janetopoulos |

It is certified that error appears in the above-identified patent and that said Letters Patent is hereby corrected as shown below:

In the Specification

Column 1, Lines 6-8, replace "The U.S. government retains certain rights in the invention according to the provisions of grants from the U.S. National Institutes of Health numbered GM28007 and GM34933." with --This invention was made with government support under GM034900 and GM028007, awarded by the National Institutes of Health. The government has certain rights in the invention.--

Signed and Sealed this
Twenty-fifth Day of August, 2020

Andrei Iancu
*Director of the United States Patent and Trademark Office*